United States Patent [19]

Maurer et al.

[11] 4,376,786
[45] Mar. 15, 1983

[54] COMBATING ARTHROPODS WITH 4-FLUORO-3-PHENOXY-BENZYL 3-ALKEN-1-YL-2,2-DIMETHYL-CYCLOPROPANECARBOXYLATES

[75] Inventors: Fritz Maurer, Wuppertal; Ingeborg Hammann, Cologne; Bernhard Homeyer, Leverkusen; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 352,688

[22] Filed: Feb. 26, 1982

[30] Foreign Application Priority Data

Mar. 19, 1981 [DE] Fed. Rep. of Germany ....... 3110725

[51] Int. Cl.[3] .................. A01N 53/00; C07C 69/743; C07C 121/75
[52] U.S. Cl. .............................. 424/304; 260/465 D; 560/124; 424/305
[58] Field of Search .................. 260/465 D; 560/124; 424/304, 305

[56] References Cited

U.S. PATENT DOCUMENTS 3,666,789  5/1972  Itaya et al. ......................... 260/468
4,218,469  8/1980  Fuchs et al. ....................... 424/304

FOREIGN PATENT DOCUMENTS 2709264  9/1978  Fed. Rep. of Germany .

Primary Examiner—Dolph H. Torrence
Attorney, Agent, or Firm—Sprung, Horn, Kramer & Woods

[57] ABSTRACT

4-Fluoro-3-phenoxy-benzyl 3-alken-1-yl-2,2-dimethyl-cyclopropanecarboxylates have the general formula

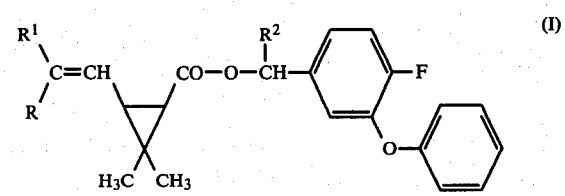

wherein
R represents alkyl or alkenyl,
$R^1$ represents hydrogen or alkyl, with the proviso that R and $R^1$ are different, and
$R^2$ represents hydrogen, cyano or alkyl, alkenyl or alkynyl having in each case up to 4 carbon atoms, are obtained if 3-alken-1-yl-2,2-dimethyl-cyclopropanecarboxylic acids of the general formula

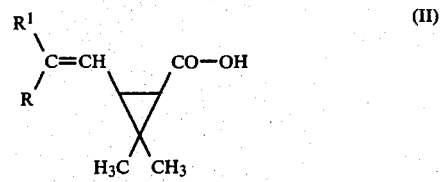

wherein
R and $R^1$ have the meaning given above, or reactive derivatives of these acids, are reacted with 4-fluoro-3-phenoxy-benzyl alcohols of the general formula

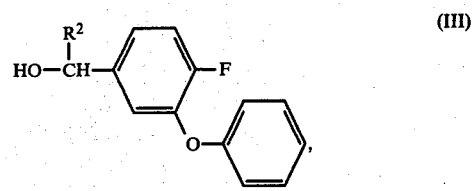

wherein
$R^2$ has the meaning given above, or with reactive derivatives of these alcohols, if appropriate in the presence of an acid acceptor and/or catalyst, and if appropriate using a diluent. The compounds of the formula (I) have a high pesticidal activity, especially against insects or acarids.

6 Claims, No Drawings

COMBATING ARTHROPODS WITH 4-FLUORO-3-PHENOXY-BENZYL 3-ALKEN-1-YL-2,2-DIMETHYL-CYCLO-PROPANECARBOXYLATES

The invention relates to certain new 4-fluoro-3-phenoxy-benzyl 3-alken-1-yl-2,2-dimethyl-cyclopropanecarboxylates, to a process for their preparation and to their use as pest-combating agents, particularly as insecticides and acaricides.

It is known that certain substituted phenoxy-benzyl cyclopropanecarboxylates, for example 3-phenoxy-benzyl 3-(2-methyl-propen-1-yl)-2,2-dimethylcyclopropanecarboxylate (phenothrin) and 3-(4-fluorophenoxy)-α-cyanobenzyl 3-(2-methyl-propen-1-yl)-2,2-dimethyl-cyclopropanecarboxylate, have insecticidal and acaricidal properties (see British patent specification Nos. 1,243,858 and 1,549,462).

However, the action of these compounds is not always satisfactory, particularly when used at low active compound concentrations or in small quantities.

The present invention now provides, as new compounds, the 4-fluoro-3-phenoxy-benzyl 3-alken-1-yl-2,2-dimethylcyclopropanecarboxylates of the general formula

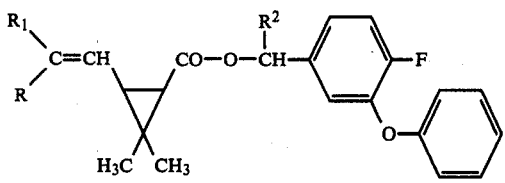

wherein
R represents alkyl or alkenyl,
$R^1$ represents hydrogen or alkyl, with the proviso that R and $R^1$ are different, and
$R^2$ represents hydrogen, cyano or alkyl, alkenyl or alkynyl having in each case up to 4 carbon atoms.

The general formula (I) includes the various possible stereoisomers and optical isomers, as well as mixtures thereof.

The present invention also provides a process for the preparation of a compound of the formula (I) in which a 3-alken-1-yl-2,2-dimethyl-cyclopropanecarboxylic acid of the general formula

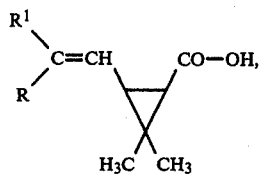

wherein
R and $R^1$ have the meanings given above, or a reactive derivative of such an acid, is reacted with a 4-fluoro-3-phenoxy-benzyl alcohol of the general formula

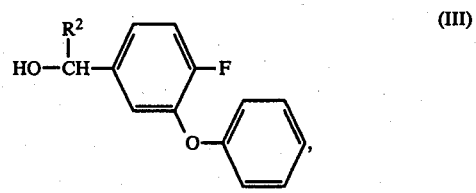

wherein
$R^2$ has the meaning given above, or with a reactive derivative of such an alcohol, if appropriate in the presence of an acid acceptor and/or a catalyst and if appropriate using a diluent.

The 4-fluoro-3-phenoxy-benzyl 3-alken-1-yl-2,2-dimethyl-cyclopropanecarboxylates of the formula (I) are distinguished by a high pesticidal activity.

Surprisingly, the compounds according to the invention exhibit a considerably greater insecticidal and acaricidal action than compounds which are known from the state of the art and are of analogous constitution and which exhibit the same direction of action.

The preferred compounds of the formula (I) are those wherein:
R represents $C_1$–$C_{25}$-alkyl or $C_2$–$C_{16}$-alkenyl,
$R^1$ represents hydrogen or methyl, with the proviso that R and $R^1$ are different, and
$R^2$ represents hydrogen or cyano.

Particularly preferred compounds of the formula (I) are those wherein:
R represent $C_1$–$C_{15}$-alkyl or $C_2$–$C_4$-alkenyl,
$R^1$ represents hydrogen or methyl, R and $R^1$ being different, and
$R^2$ represents hydrogen or cyano.

In a preferred variant (a) of the process for the preparation of the compounds of the formula (I), a 3-alken-1-yl-2,2-dimethyl-cyclopropanecarboxylic acid chloride of the general formula

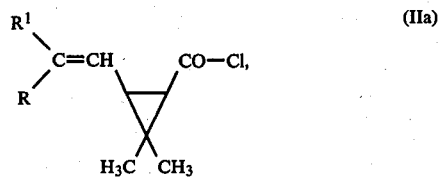

wherein
R and $R^1$ have the meanings given above, is reacted with a 4-fluoro-3-phenoxy-benzyl alcohol of the formula (III) above, in the presence of an acid acceptor and using a diluent.

In a further preferred process variant (b), for the preparation of a compound of the formula (I) in which $R^2$ represents cyano, an acid chloride of the formula (IIa) above is reacted with 4-fluoro-3-phenoxy-benzaldehyde, of the formula

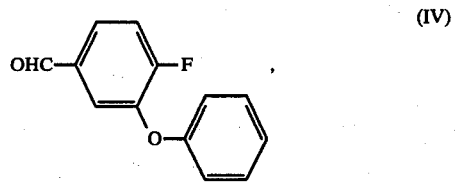

and at least an equimolar quantity of an alkali metal cyanide (especially sodium cyanide or potassium cyanide), in the presence of water and of a diluent which is virtually immiscible with water, and, if appropriate, in the presence of a catalyst.

The lower alkyl esters of the carboxylic acids of the formula (II) may be mentioned as further reactive derivatives of these carboxylic acids, which esters can be reacted with alcohols of the formula (III), according to customary methods.

Alkali metal salts, alkaline earth metal salts or ammonium salts of the carboxylic acids (II) can also be reacted with benzyl halides, which are derived from the benzyl alcohols of the formula (III), to give compounds of the formula (I).

If, for example, 3-propen-1-yl-2,2-dimethyl-cyclopropanecarboxylic acid chloride and in process variant (a) 4-fluoro-3-phenoxy-benzyl alcohol or in process variant (b) sodium cyanide and 4-fluoro-3-phenoxybenzaldehyde are used as starting materials, the reactions proceeding in the two process variants can be represented by the following equations:

(a) 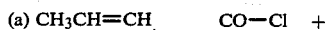

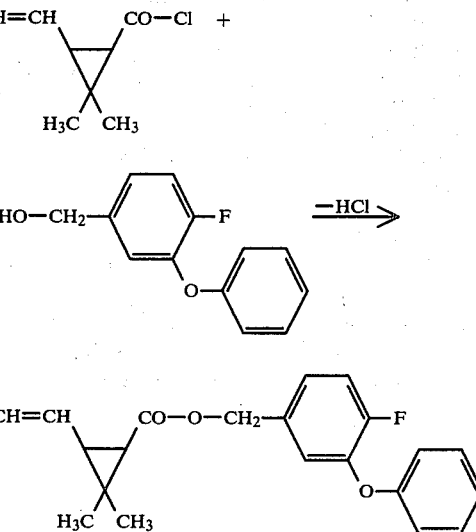

(b) 

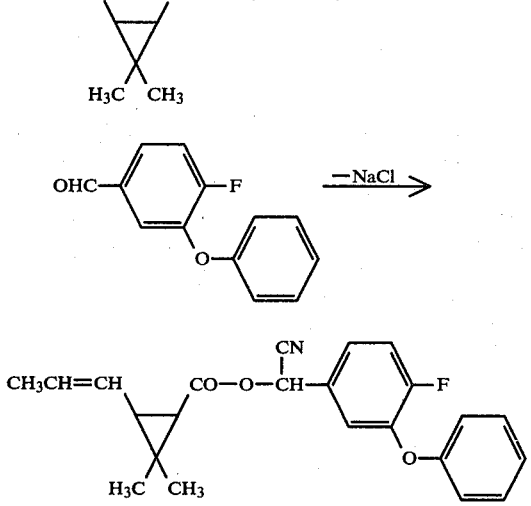

Formula (II) gives a definition of the 3-alken-1-yl-2,2-dimethyl-cyclopropanecarboxylic acids to be used as starting materials and formula (IIa) gives a definition of the corresponding acid chlorides. In these formulae, R and $R^1$ preferably have those meanings which have been mentioned as preferred in the definition of R and $R^1$ in formula (I).

The following may be mentioned as examples of the starting compounds of the formulae (II) and (IIa): 3-propen-1-yl-, 3-buten-1-yl-, 3-penten-1-yl-, 3-hexen-1-yl-, 3-hepten-1-yl-, 3-octen-1-yl, 3-nonen-1-yl-, 3-decen-1-yl-, 3-undecen-1-yl-, 3-dodecen-1-yl-, 3-tridecen-1-yl-, 3-tetradecen-1-yl-, 3-pentadecen-1-yl-, 3-hexadecen-1-yl-, 3-heptadecen-1-yl-, 3-octadecen-1-yl-, 3-(2-methyl)-buten-1-yl-, 3-(2-methyl)-penten-1-yl-, 3-(2-methyl)-hexen-1-yl-, 3-(2-methyl)-hepten-1-yl-, 3-(2-methyl)-octen-1-yl-, 3-(2-methyl)-nonen-1-yl-, 3-(2-methyl)-decen-1-yl-, 3-(2-methyl)-undecen-1-yl-, 3-(2-methyl)-dodecen-1-yl-, 3-(2-methyl)-tridecen-1-yl-, 3-(2-methyl)-tetradecen-1-yl-, 3-(2-methyl)-pentadecen-1-yl-, 3-(2-methyl)-hexadecen-1-yl-, 3-(2-methyl)-heptadecen-1-yl-, 3-(1-methyl)-octadecen-1-yl-, 3-butadien-1,3-yl-, 3-pentadien-1,3-yl-, 3-(4-methyl)-pentadien-1,3-yl- and 3-(4-methyl)-penten-1-yl-2,2-dimethyl-cyclopropanecarboxylic acid and the corresponding acid chlorides.

3-Alken-1-yl-2,2-dimethyl-cyclopropanecarboxylic acids of the formula (II), corresponding acid chlorides of the formula (IIa) or corresponding lower alkyl esters are known and can be prepared according to processes which are in themselves known (see British patent specification No. 1,413,491 and U.S. Pat. Nos. 3,847,944, 3,954,814 and 3,998,868).

Formula (III) gives a definition of the 4-fluoro-3-phenoxy-benzyl alcohols also to be used as staring materials. In this formula, $R^2$ preferably represents hydrogen or cyano.

4-Fluoro-3-phenoxy-benzyl alcohol and 4-fluoro-3-phenoxy-α-cyano-benzyl alcohol may be mentioned as examples.

Compounds of the formula (III) are already known (see U.S. Pat. No. 4,218,469).

The 4-fluoro-3-phenoxy-benzaldehyde of the formula (IV), which can be used as a starting material, is also known (see U.S. Pat. No. 4,218,469).

All variants of the process for the preparation of the compounds of the formula (I) are preferably carried out using a diluent. Virtually any inert organic solvent is suitable as a diluent. These include, as preferences, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene; ethers, such as diethyl ether, dibutyl ether, glycol dimethyl ether, diglycol dimethyl ether, tetrahydrofuran and dioxane; ketones, such as acetone, methyl ethyl ketone, methyl isopropyl ketone and methyl isobutyl ketone; esters, such as methyl acetate and ethyl acetate; nitriles, such as acetonitrile and propionitrile; amides, such as dimethylformamide, dimethylacetamide and N-methylpyrrolidone; and dimethylsulphoxide, tetramethylenesulphone or hexamethylphosphoric acid triamide.

Variant (a) of the process according to the invention is preferably carried out in the presence of an acid acceptor. Any of the customary acid-binding agents can be used as the acid acceptor. Alkali metal carbonates and alcoholates, such as sodium carbonate, potassium carbonate, sodium methylate or ethylate and potassium methylate or ethylate, and also aliphatic, aromatic or heterocyclic amines, for example triethylamine, trimethylamine, dimethylaniline, dimethylbenzylamine, pyridine, diazabicyclooctane, diazabicyclononene or diazabicycloundecene, have proved particularly suitable.

Variant (b) of the process according to the invention is carried out in the presence of water and of an organic solvent, preferably one of the abovementioned organic solvents, provided that it is immiscible with water. The abovementioned hydrocarbons, in particular, are suitable for this purpose.

Compounds which are suitable for the transfer of anions from water into organic solvents are preferably used as the catalysts in the process variant(b). Benzyltriethyl-ammonium hydrogen sulphate, benzyl-triethylammonium chloride, tetrabutylammonium bromide and methyl-trioctyl-ammonium chloride (Aliquat 336) are examples of these catalysts.

In all process variants, the reaction temperature can be varied within a broad range. In general, the reaction is carried out at a temperature between 0° and 100° C., preferably at from 10° to 50° C.

The process according to the invention is carried out, in general, under normal pressure. The starting materials are customarily employed in equimolar quantities for carrying out the process according to the invention: an excess of one or the other of the reactants has no substantial advantages. The starting materials are combined in suitable diluents and, if appropriate after the addition of an acid acceptor and/or a catalyst, are stirred until the end of the reaction.

The working-up can be carried out according to customary methods, for example by diluting the reaction mixture, if appropriate, with water and/or a water-immiscible organic solvent, for example toluene, and separating off the organic phase, washing it with water, drying it and filtering it, and carefully distilling off the solvent, under reduced pressure and at moderately elevated temperature, from the filtrate ("incipient distillation").

The active compounds are well tolerated by plants, have a favorable level of toxicity to warm blooded animals, and are suitable for combating arthropod pests, especially insects and arachnids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.:

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euprotis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Mucsa spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans or fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol, as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their formulations of the types that are commercially available and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by micro-organisms.

The active compounds according to the invention can furthermore be present in their formulations of the types that are commercially available and in the use forms, prepared from these formulations, as a mixture with synergistic agents. Synergistic agents are compounds which increase the action of the active compounds, without it being necessary for the synergistic agent added to be active itself.

The active compound content of the use forms prepared from the formulations of the types that are commercially available can vary within wide limits. The active compound concentration of the use forms can be from 0.0000001 to 100% by weight of active compound, preferably between 0.0001 and 1% by weight.

The compounds may be employed in a customary manner appropriate for the use forms.

When used against pests harmful to health and pests of stored products, the active compounds are distinguished by an excellent residual action on wood and clay as well as a good stability to alkali on limed substrates.

The active compounds according to the invention are also suitable for combating ectoparasites and endoparasites in the field of veterinary medicine.

The active compounds according to the invention are used in a known manner in the veterinary sector, such as by oral administration, for example in the form of tablets, capsules, drinks and granules, by dermal application, for example by dipping, spraying, pouring on, spotting on and dusting, and by parenteral administration, for example in the form of an injection.

The present invention thus provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites (for example insects or ticks) which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

The substituted cyclopropanecarboxylic acid chlorides to be used as starting materials were prepared, for example, as follows:

EXAMPLE 1

1st stage:

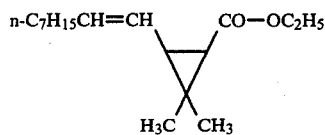

64.5 g of a 15% strength solution of butyl-lithium in n-hexane were added dropwise to a suspension of 68.3 g (0.15 mol) of n-octyl-triphenylphosphonium bromide in 300 ml of absolute tetrahydrofuran at 0°–5° C., with the exclusion of air. After one hour, 25.5 g (0.15 mol) of ethyl 2-formyl-3,3-dimethylcyclopropanecarboxylate were slowly added, and the mixture was further stirred for 18 hours at room temperature. The mixture was shaken after the addition of 400 ml of toluene and 300 ml of water, the water was separated off and the organic phase was washed once again with 200 ml of water. The toluene solution was then dried over sodium sulphate and the solvent was distilled off in vacuo. The residue was stirred with 300 ml of petroleum ether (40°–60° C.), the solution was filtered off from the undissolved triphenylphosphine oxide, and the filtrate was again concentrated by evaporation in vacuo. The residue was distilled in vacuo. 22.6 g (57% of theory) of ethyl 2-(1-nonen-1-yl)-3,3-dimethylcyclopropanecarboxylate with a boiling point of 90° C./0.01 mm Hg were thus obtained.

The following compounds of the formula

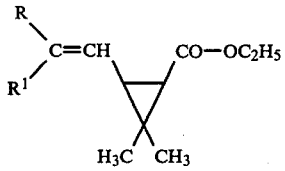

could be prepared in an analogous manner:

TABLE I

| R | $R^1$ | Yield (% of theory) | Boiling point (°C./mm Hg) |
|---|---|---|---|
| n-$C_5H_{11}$ | H | 60 | 92–95/0.5 |
| n-$C_3H_7$ | H | 56 | 72–75/0.3 |
| $C_2H_5$ | H | 59 | 108–110/10 |
| $CH_3$ | H | 60 | 93–96/10 |
| n-$C_4H_9$ | H | 48 | 63–65/0.01 |
| n-$C_6H_{13}$ | H | 54 | 92–94/0.2 |
| n-$C_{15}H_{31}$ | H | 57 | 170–175/0.1 |
| $(CH_3)_2C=CH$ | H | 66 | 70/0.1 |
| n-$C_8H_{17}$ | H | 65 | 110/0.1 |
| n-$C_5H_{11}$ | $CH_3$ | 57 | 90–93/0.2 |
| $(CH_3)_2CH-CH_2$ | H | | |
| n-$C_4H_9$ | $CH_3$ | | |
| n-$C_3H_7$ | $CH_3$ | 49 | 76/0.1 |
| $C_2H_5$ | $CH_3$ | | |
| $(CH_3)_2CH-CH_2-CH_2$ | H | | |
| n-$C_6H_{13}$ | $CH_3$ | | |

2nd stage:

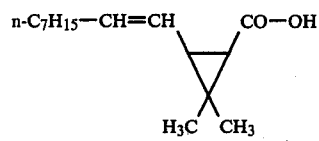

A mixture of 5.6 g (0.1 mol) of potassium hydroxide, 45 ml of water, 45 ml of ethanol and 22 g (0.083 mol) of ethyl 2-(1-nonen-1-yl)-3,3-dimethylcyclopropanecarboxylate was boiled under reflux for 5 hours, 150 ml of water were then added to the mixture, and the mixture was extracted twice with 100 ml of ether. The aqueous phase was acidifed and the product was extracted by shaking with methylene chloride (twice 100 ml). After the extracts had been dried over sodium sulphate, the solvent was distilled off in vacuo. 17 g (86% of theory) of 2-(1-nonen-1-yl)-3,3-dimethylcyclopropanecarboxylic acid remained in the form of a yellow oil.

The following compounds of the formula

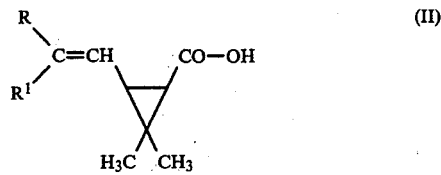

could be prepared in an analogous manner.

TABLE 2

| R | $R^1$ | Yield (% of theory) |
|---|---|---|
| n-$C_5H_{11}$ | H | 93 |
| n-$C_3H_7$ | H | 92 |
| $C_2H_5$ | H | 77 |
| $CH_3$ | H | 86 |
| n-$C_4H_9$ | H | 80 |
| n-$C_6H_{13}$ | H | 82 |
| n-$C_{15}H_{31}$ | H | 85 |
| $(CH_3)_2C=CH$ | H | 99 |
| n-$C_8H_{17}$ | H | 84 |
| n-$C_5H_{11}$ | $CH_3$ | 86 |
| $(CH_3)_2CH-CH_2$ | H | |
| n-$C_4H_9$ | $CH_3$ | |
| n-$C_3H_7$ | $CH_3$ | |
| $C_2H_5$ | $CH_3$ | |
| $(CH_3)_2CH-CH_2-CH_2$ | H | |
| n-$C_6H_{13}$ | $CH_3$ | |

3rd stage:

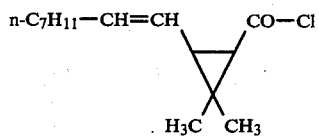

2 drops of dimethylformamide and then 11.2 g (0.095 mol) of thionyl chloride were added to a solution of 16.8 g (0.07 mol) of 2-(1-nonen-1-yl)-3,3-dimethylcyclopropane acid in 80 ml of methylene chloride. The mixture was then boiled under reflux for 1 hour, the solvent is distilled off in vacuo and the residue was distilled in vacuo. 16 g (89% of theory) of 2-(1-nonen-1-yl)-3,3-dimethylcyclopropanecarboxylic acid chloride with a boiling point of 110°/0.5 mm Hg were obtained in this manner.

The following compounds of the formula

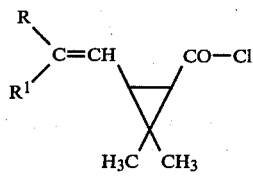

could be prepared in an analogous manner:

TABLE 3

| R | $R^1$ | Yield (% of theory) | Boiling point (°C./mm Hg) |
| --- | --- | --- | --- |
| n-C$_5$H$_{11}$ | H | 83 | 70/0.1 |
| n-C$_3$H$_7$ | H | 85 | 48/0.05 |
| C$_2$H$_5$ | H | 84 | 55/0.5 |
| CH$_3$ | H | 86 | 51/1 |
| n-C$_4$H$_9$ | H | 91 | 65/0.3 |
| n-C$_6$H$_{13}$ | H | 82 | 85/0.2 |
| n-C$_{15}$H$_{31}$ | H | 91 | 191/0.4 |
| (CH$_3$)$_2$C=CH | H | 85 | 81/0.2 |
| n-C$_8$H$_{17}$ | H | 83 | 105/0.01 |
| n-C$_5$H$_{11}$ | CH$_3$ | 84 | 84/0.1 |
| (CH$_3$)$_2$CH—CH$_2$ | H | | |
| n-C$_4$H$_9$ | CH$_3$ | | |
| n-C$_3$H$_7$ | CH$_3$ | 85 | 72/0.2 |
| C$_2$H$_5$ | CH$_3$ | | |
| (CH$_3$)$_2$CH—CH$_2$—CH$_2$ | H | | |
| n-C$_6$H$_{13}$ | CH$_3$ | | |

EXAMPLE 2

End products were produced as follows:

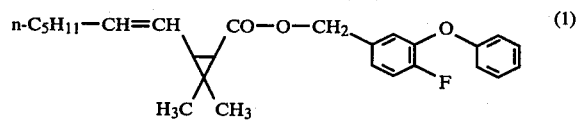

A solution of 2-(1-hepten-1-yl)-3,3-dimethylcyclopropanecarboxylic acid chloride in 10 ml of toluene was added dropwise to a solution of 8.8 g (0.04 mol) of 4-fluoro-3-phenoxy-benzyl alcohol and 4.2 g (0.041 mol) of triethylamine in 80 ml of toluene. The reaction mixture was further stirred for 18 hours at room temperature and was then washed with twice 50 ml of water. The organic phase was dried over sodium sulphate and concentrated by evaporation in vacuo; the residue was subjected to incipient distillation in a high vacuum. 15.2 g (93% of theory) of 4-fluoro-3-phenoxy-benzyl 2-(1-hepten-1-yl)-3-3-dimethylcyclopropanecarboxylate were thus obtained in the form of a yellow oil with a refractive index $n_D^{20}$: 1.5302.

EXAMPLE 3

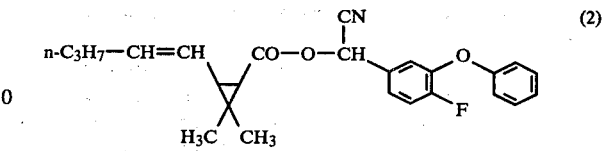

A solution of 2.05 g (0.042 mol) of sodium cyanide in 5 ml of water and, subsequently, a solution of 5.6 g (0.028 mol) of 2-(1-penten-1-yl)-3,3-dimethylcyclopropanecarboxylic acid chloride in 6 ml of toluene were added to a mixture of 40 ml of toluene, 6 g (0.028 mol) of 4-fluoro-3-phenoxybenzaldehyde and 0.3 g of triethylbenzylammonium chloride. The reaction mixture was then further stirred for 18 hours at room temperature and was then washed with twice 50 ml of water. The organic phase was dried over sodium sulphate and concentrated by evaporation in vacuo; the residue was subjected to incipient distillation in a high vacuum. 10 g (88% of theory) of cyano-(4-fluoro-3-phenoxybenzyl) 2-(1-penten-1-yl)-3,3-dimethyl-cyclopropanecarboxylate remained in the form of a yellow viscous oil with a refractive index $n_D^{20}$: 1.5383.

The following compounds of the formula

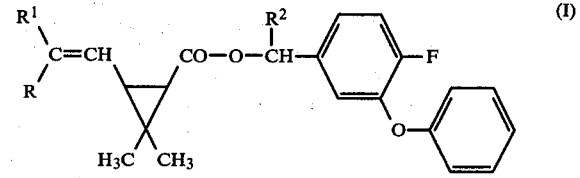

could each be prepared by a method analogous to that described in Example 2 or 3:

TABLE 4

| Compound No. | R | $R^1$ | $R^2$ | Yield (% of theory) | Refractive index: |
| --- | --- | --- | --- | --- | --- |
| 3 | n-C$_5$H$_{11}$ | H | CN | 84 | $n_D^{20}$: 1.5312 |
| 4 | C$_2$H$_5$ | H | CN | 92 | $n_D^{20}$: 1.5395 |
| 5 | CH$_3$ | H | CN | 91 | $n_D^{19}$: 1.5448 |
| 6 | n-C$_4$H$_9$ | H | CN | 73 | $n_D^{19}$: 1.5357 |
| 7 | n-C$_6$H$_{13}$ | H | CN | 94 | $n_D^{19}$: 1.5293 |
| 8 | n-C$_{15}$H$_{31}$ | H | CN | 97 | $n_D^{22}$: 1.5148 |
| 9 | (CH$_3$)$_2$C=CH | H | CN | 70 | $n_D^{25}$: 1.5583 |
| 10 | n-C$_7$H$_{15}$ | H | CN | 95 | $n_D^{25}$: 1.5239 |
| 11 | n-C$_8$H$_{17}$ | H | CN | 91 | $n_D^{23}$: 1.5227 |
| 12 | n-C$_5$H$_{11}$ | CH$_3$ | CN | 89 | $n_D^{19}$: 1.5298 |
| 13 | (CH$_3$)$_2$CH—CH$_2$ | H | CN | | |
| 14 | CH$_3$ | H | H | | |
| 15 | C$_2$H$_5$ | H | H | | |
| 16 | n-C$_3$H$_7$ | H | H | | |
| 17 | n-C$_4$H$_9$ | H | H | | |
| 18 | n-C$_4$H$_9$ | CH$_3$ | CN | | |
| 19 | n-C$_3$H$_7$ | CH$_3$ | CN | 99 | $n_D^{21}$: 1.5355 |

TABLE 4-continued

| Compound No. | R | $R^1$ | $R^2$ | Yield (% of theory) | Refractive index: |
|---|---|---|---|---|---|
| 20 | $C_2H_5$ | $CH_3$ | CN | | |
| 21 | $(CH_3)_2CH-CH_2-CH_2$ | H | CN | | |
| 22 | $n-C_6H_{13}$ | $CH_3$ | CN | | |
| 23 | $n-C_5H_{11}$ | $CH_3$ | H | | |

In the foregoing tables only those compounds have actually been prepared for which yields and/or physical data are provided.

The pesticidal activity of the compounds of this invention is illustrated by the following biotest examples.

In these examples, the compounds according to the present invention are each identified by the number (given in brackets) from Examples 2 and 3 and Table 4.

EXAMPLE 4

Drosophila test
Solvent: 3 parts by weight of acetone
Emulsifer: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

1 cm³ of the preparation of the active compound was pipetted onto a filter paper disc (7 cm diameter). The wet disc was placed over the opening of a glass vessel containing 50 vinegar flies (*Drosophila melanogaster*) and was covered with a glass plate.

After the specified periods of time, the destruction in % was determined. 100% meant that all the flies had been killed; 0% meant that none of the flies had been killed.

In this test, for example, the following compounds showed a superior activity compared with the prior art: (5), (4), (2), (6), (3), (12), (7), (10) and (11).

EXAMPLE 5

Phaedon larvae test
Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of the active compound of the desired concentration and were infested with mustard beetle larvae (*Phaedon cochleariae*), as long as the leaves were still wet.

After the specified periods of time, the destruction in % was determined. 100% meant that all the beetle larvae had been killed; 0% meant that none of the beetle larvae had been killed.

In this test, for example, the following compounds showed a superior activity compared with the prior art: (5), (9), (4), (2), (6), (12), (7), (10), (11) and (8).

EXAMPLE 6

Tetranychus test (resistant)
Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Phaseolus vulgaris*) which were heavily infested with the common spider mite or two-spotted spider mite (*Tetranychus urticae*) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In this test, for example, the following compounds showed a superior activity compared with the prior art: (4), (2), (6) and (12).

EXAMPLE 7

Critical concentration test/soil insects
Test insect: Phorbia antiqua grubs (in the soil)
Solvent 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l), being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and the live test insects. The degree of effectiveness was 100% if all the test insects had been killed and was 0% if just as many test insects were still alive as in the case of the untreated control.

In this test, for example, the following compounds showed a superior action compared with the prior art: (3), (2), (4) and (5).

EXAMPLE 8

Critical concentration test/soil insects
Test insect: *Agrotis segetum* larvae (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l), being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and the live test insects. The degree of effectiveness was 100% if all the test insects had been killed and was 0% if just as many test insects were still alive as in the case of the untreated control.

In this test, for example, the following compounds showed a superior action compared with the prior art: (4), (5), (6) and (9).

EXAMPLE 9

$LT_{100}$ test for Diptera
Test insects: *Aedes aegypti*
Number of test insects: 20
Solvent: Acetone The active compound was taken up in the solvent at a rate of 2 g per 1000 ml of solvent. The solution thus obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound used. The stated number of test insects was then placed in the Petri dish and the dish was covered with a glass lid.

The condition of the test insects was continuously checked. The time which was necessary for 100% knockdown effect was determined.

In this test, for example, the following compounds showed a superior action compared with the prior art: (2), (4), (5) and (6).

EXAMPLE 10

$LT_{100}$ test
Test insects: *Sitophilus granarius*
Number of test insects: 20
Solvent: Acetone The active compound was taken up in the solvent at a rate of 2 g per 1000 ml of solvent. The solution thus obtained was diluted with further solvent to the desired concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound used. The stated number of test insects was then placed in the Petri dish and the dish was covered with a glass lid.

The condition of the test insects was checked 3 days after the start of the tests. The destruction in % was determined. 100% meant that all the test insects had been killed; 0% meant that none of the test insects had been killed.

In this test, for example, the following compounds showed a superior action compared with the prior art: (12), (7), (6), (5), (4), (2) and (3).

EXAMPLE 11

Test with *Boophilus microplus* resistant
Solvent: 35 parts by weight of ethylene glycol monomethyl ether 35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 adult specimens of *Boophilus microplus* res. were immersed for 1 minute in the active compound preparation to be tested. After transfer to plastic beakers and storage in a climatically controlled chamber, the degree of destruction was determined.

In this test, for example, the following compounds showed a superior action compared with the prior art: (1), (3), (6), (7) and (9).

EXAMPLE 12

Test with *Lucilia cuprina* res. larvae
Emulsifier: 35 parts by weight of ethylene glycol monomethyl ether 35 parts by weight of nonylphenol polyglycol ether To produce a suitable preparation of active compound, three parts by weight of active compound were mixed with seven parts by weight of the abovementioned solvent mixture and the concentrate thus obtained was diluted with water to the particular desired concentration.

About 20 *Lucilia cuprina* res. larvae were introduced into a test tube which contained approx. 1 cm³ of horse muscle and 0.5 ml of the preparation of active compound. After 24 hours, the degree of destruction was determined.

In this test, for example, the following compounds showed a superior action compared with the prior art: (3), (6), (7) and (9).

It will be appreciated that the instant specification and examples are set forth by way of illustration and not limitation, and that various modifications and changes may be made without departing from the spirit and scope of the present invention.

We claim:

1. A 4-fluoro-3-phenoxy-benzyl 3-alken-1-yl-2,2-dimethyl-cyclopropanecarboxylate of the formula

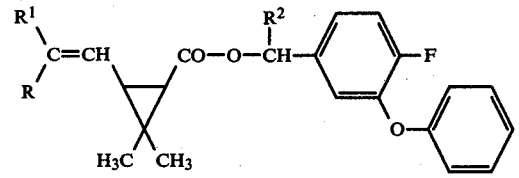

wherein
R is alkyl or alkenyl,
$R^1$ is hydrogen or alkyl different from R, and
$R^2$ is hydrogen, cyano, or alkyl, alkenyl or alkynyl each having up to 4 carbon atoms.

2. A compound according to claim 1, wherein
R is $C_1-C_{25}$-alkyl or $C_2-C_{16}$-alkenyl,
$R^1$ is hydrogen, may be methyl when R is not methyl, and
$R^2$ is hydrogen or cyano.

3. A compound according to claim 2, wherein
R is $C_1-C_{15}$-alkyl or $C_2-C_4$-alkenyl.

4. A pesticidal composition comprising a pesticidally effective amount of a compound according to claim 1 in admixture with a diluent.

5. A composition according to claim 4, characterized in that it contains from 0.1 to 95% of the active compound, by weight.

6. A method of combating pests comprising applying to the pests, or to a habitat thereof, a pesticidally effective amount of a compound according to claim 1.

* * * * *